United States Patent [19]

Yu et al.

[11] 4,216,224

[45] Aug. 5, 1980

[54] METHODS AND COMPOSITIONS FOR TREATING PSORIASIS WITH RETINOYL COMPOUNDS

[76] Inventors: Ruey J. Yu, 4 Lindenwold Ave., Ambler, Pa. 19002; Eugene J. Van Scott, 1138 Sewell La., Rydal, Pa. 19046

[21] Appl. No.: 944,980

[22] Filed: Sep. 22, 1978

[51] Int. Cl.$^2$ ............................................ A61K 31/325
[52] U.S. Cl. .................................... 424/286; 424/305; 424/313; 424/320; 424/324; 424/344; 260/557 R; 260/513.5; 560/115; 560/128; 562/507
[58] Field of Search ................. 424/286, 320; 560/507

[56] References Cited

PUBLICATIONS

Jama, 3-10-69, vol. 207, No. 10, pp. 1863-1868.

*Primary Examiner*—Leonard Schenkman
*Attorney, Agent, or Firm*—Le Blanc, Nolan, Shur & Nies

[57] ABSTRACT

Compositions and methods for treating the symptoms of psoriasis consisting of topical application of a solution, gel, lotion, cream or ointment containing as a principal active ingredient one or more retinoyl compounds is disclosed. The active ingredient consists of one or more compounds which are retinoyl esters of a hydroxy acid, a hydroxy amide, or a hydroxy acid ester, or a retinoyl carbamic or thiocarbamic acid derivative. The composition of this invention may include a single member of the above active ingredients present in a total amount of from 0.01 to 5% by weight of the total composition, or a plurality thereof present in a preferred concentration of from 0.02 to 2% by weight of the total composition.

44 Claims, No Drawings

METHODS AND COMPOSITIONS FOR TREATING PSORIASIS WITH RETINOYL COMPOUNDS

This application is related to our co-pending patent application Ser. No. 869,351 filed Jan. 13, 1978, and entitled "Alpha Hydroxyretinoic, Alpha Ketoretinoic Acid and Mixtures and Their Use in Treating Skin Conditions."

Retinoic acid is known to be useful in the treatment of acne as disclosed in U.S. Pat. No. 3,729,568. In addition, in our previous U.S. Pat. No. 3,932,665 it was disclosed that retinal was useful in the treatment of acne without causing a worsening or irritation or peeling of the skin, a condition observed with the use of retinoic acid.

In our above-identified U.S. patent application Ser. No. 869,351, filed Jan. 13, 1978, it was disclosed that alpha-hydroxyretinoic acids, alpha-ketoretinoic acid and mixtures thereof are useful in treating epithelial tissue that exhibits a disturbance in its keratinization. Said compounds were disclosed as active in the treatment of such conditions as dry skin, ichthyosis, dandruff, acne, psoriasis, eczema, mycosis fungoides, and even active in alleviating the symptoms of skin cancer.

It has now been discovered that certain additional compounds broadly described as retinoyl derivatives are active in the treatment of psoriasis by topical application. The compounds of this invention have been found to be effective in alleviating the symptoms of psoriasis without causing unacceptable or painful skin irritation, burning or the like, and in addition, that the compounds of this invention are relatively non-toxic at the acceptable level of dosage for topical application.

In accordance with the present invention, the retinoyl compounds which are incorporated in therapeutic compositions for topical application to alleviate the symptoms of psoriasis are of two classes.

The first class of compounds is a retinoyl ester of a hydroxy acid, a hydroxy amide or a hydroxy acid ester, as shown by:

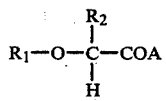

$R_1$: Retinoyl ($C_{20}H_{27}O$)
$R_2$: H, alkyl or aryl of 1 to 9 carbon atoms
A: OH, $NH_2$ or alkoxyl of 1 to 9 carbon atoms Preferred retinoyl hydroxy acids and derivatives which are useful for the topical treatment of psoriasis are listed below:
1. Methyl retinoyl glycolate
2. Ethyl retinoyl glycolate
3. Retinoyl glycolic acid
4. Retinoyl lactamide
5. Ethyl retinoyl lactate
6. Diethyl retinoyl tartrate
7. Triethyl retinoyl citrate
8. Ethyl retinoyl mandelate
9. Isoamyl retinoyl mandelate
10. Retinoyl phenyllactic acid
11. Retinoyl salicylic acid
12. Methyl retinoyl salicylate
13. Retinoyl salicylamide The second class of retinoyl compounds is a carbamic or thiocarbamic acid derivative, as shown by the following chemical structures:

$R_1$: Retinoyl ($C_{20}H_{27}O$)
$R_3$: H, alkyl or aryl of 1 to 20 carbon atoms
B: O or S These retinoyl carbamic or thiocarbamic acids may be incorporated in therapeutic compositions as either free acids amides or salts formed with organic bases or inorganic alkalis.

Representative retinoyl carbamic or thiocarbamic acids which are useful for the topical treatment of psoriasis are listed below:
1. N-methyl-N-retinoyl-carbamic acid
2. N-ethyl-N-retinoyl-carbamic acid
3. N-propyl-N-retinoyl-carbamic acid
4. N-butyl-N-retinoyl-carbamic acid
5. N-allyl-N-retinoyl-carbamic acid
6. N-phenyl-N-retinoyl-carbamic acid
7. N-octadecyl-N-retinoyl-carbamic acid
8. N-m-chlorophenyl-N-retinoyl-carbamic acid
9. N-p-tolyl-N-retinoyl-carbamic acid
10. N-m-tolyl-N-retinoyl-carbamic acid
11. N-o-tolyl-N-retinoyl-carbamic acid
12. N-methyl-N-retinoyl-thiocarbamic acid
13. N-ethyl-N-retinoyl-thiocarbamic acid
14. N-butyl-N-retinoyl-thiocarbamic acid
15. N-allyl-N-retinoyl-thiocarbamic acid
16. N-phenyl-N-retinoyl-thiocarbamic acid
17. N-cyclohexyl-N-retinoyl-thiocarbamic acid
18. N-cyclohexyl-N-retinoyl-N'-cyclohexyl carbamic amide.

Accordingly, it is an object of this invention to provide retinoyl compounds which are active in a pharmaceutical acceptable carrier for topical application to alleviate the symptoms of psoriasis in humans.

It is another object of this invention to provide a class of compounds which may be incorporated in a pharmaceutically acceptable carrier which when topically applied to the lesions of psoriasis will alleviate the symptoms thereof.

it is yet another object of this invention to provide a method for treating psoriasis with retinoyl esters of hydroxy acids, hydroxy amides, or hydroxy acid esters, retinoyl carbamic or thiocarbamic acid derivatives in a pharmaceutically acceptable carrier by topical application.

It is yet another object of this invention to provide a method for synthesizing retinoyl esters of hydroxy acids, hydroxy amides, and retinoyl carbamic or thiocarbamic acid derivatives useful by topical application in treatment of psoriasis.

These and other objects will become readily apparent with reference to the following description.

PREPARATION OF THE THERAPEUTIC COMPOSITIONS

In order to prepare the compositions of this invention at least one of the aforementioned retinoyl compounds is initially dissolved in a solvent such as ethanol or acetone. The solution thus prepared may then be admixed in a conventional manner with commonly available cream or ointment bases such as hydrophilic ointment (USP) or petrolatum (USP). The concentration of the compound ranges from 0.01 to 5.0 percent by weight of the total composition. The preferred concentration range, however, is from 0.02 to about 2 percent.

If desired, two or more of the aforementioned compounds may be admixed as described above to form a composition of this invention. In this instance it is preferred that the concentration of the compounds not exceed about 2 percent by weight of the total composition.

Ethanol or acetone solvent used to initially dissolve the retinoyl compound of this invention may have a concentration of from 1 to 20 percent by volume of the total composition. The preferred concentration thereof, however, is about 5 percent by volume of the total composition.

The therapeutic ointments of this invention, prepared as described above, may be stored in ointment jars.

The retinoyl compounds of this invention may also be utilized in a solution, gel or lotion form. A typical solution utilizing the compounds of this invention comprises at least one of the above-named compounds dissolved directly in a mixture of water, ethanol and propylene glycol in a volume ratio of preferably 20:60:20, respectively. The ratio of each vehicle may vary, however the preferred concentrations of water and propylene glycol should not exceed 50 percent and 30 percent respectively. When solutions are formulated according to this invention, the compound concentration may be from 0.01 to 5.0 percent by weight as above. In addition, a concentration of from 0.1 to 2.0 percent is preferred. One or more of the compounds may also be admixed to a total concentration not exceeding about 2.0 percent by weight.

A typical gel preparation of this invention utilizes at least one of the above compounds, dissolved directly in a mixture of water, ethanol and propylene glycol in a volume ratio of 20:70:10 respectively. A gelling agent such as hydroxyethylcellulose, hydroxypropylcellulose or hydroxypropylmethylcellulose is then added to the mixture with agitation. The concentration of the gelling agent may range from 0.1 to 5 percent by weight of the total composition. The preferred concentration, however, is from 0.5 to 2 percent.

A typical lotion containing the retinoyl compounds of this invention may be prepared as follows. At least one of the retinoyl compounds is dissolved in ethanol, and the solution is admixed with a lotion prepared from mineral oil, cottonseed oil, isopropyl myristate and water with a surfactant such as sorbitan sesquioleate.

In an alternative way of preparing the therapeutic compositions, one of the aforementioned retinoyl compounds of the present invention may also be directly incorporated into the composition without utilizing a solvent for dissolution.

The following examples are illustrative of formulations of compositions according to this invention. Although the examples utilize a named compound, the examples are not intended to be limited to the specific compound named, but any member of the above-described groups of retinoyl compounds or combination thereof could be substituted therefor within the scope of this invention.

It should be noted that certain all-trans-retinoic acid esters and amides are described in U.S. Pat. No. 4,055,659 by Gander et al., which patent issued Oct. 25, 1977. These materials are described as useful in the treatment of acne or other skin related disorders. This patent also describes methods of synthesizing such compounds. The following is a description of the method of synthesizing the compounds of this invention as well as methods of formulating a therapeutic composition containing said compounds.

EXAMPLE 1

Synthesis of Ethyl Retinoyl Lactate

The following procedure may be used for the synthesis of all retinoyl acid derivatives.

All-trans-retinoic acid 1 gm is dissolved in 150 ml of anhydrous benzene, and 5 ml of ethyl lactate is added to the solution. While stirring is continued dry hydrogen chloride gas is passed into the above reaction mixture until the solution is saturated with HCl gas (approximately 20 minutes). The orange reddish mixture is sealed with a stopper, and is allowed to react at room temperature for 16 hours. The reaction mixture is then successively washed with 200 ml of water, 200 ml of 5% sodium bicarbonate solution and 200 ml of saturated sodium chloride solution. The benzene layer which contains the product is dried over anhydrous sodium sulfate, and is evaporated at 35° C. in vacuum to give 0.9 gm of reddish syrup. Ethyl retinoyl lactate thus synthesized is practically pure as shown by infrared spectroscopy and by thin-layer chromatography with a mobility of 0.87 on a solvent system of methanol:benzene, 1:3.

EXAMPLE 2

A water-in-oil cream may be prepared as follows:

| Part A: | Sorbitan sesquileate | 5 gm |
|---|---|---|
|  | Petrolatum | 10 gm |
|  | Mineral oil | 15 gm |
|  | Beeswax | 10 gm |
|  | Isopropyl myristate | 10 gm |
| Part B: | Water | 42 ml |
|  | Propylene glycol | 5 ml |
|  | Sorbitol | 3 gm |

Heat Part A to 75° C., and heat Part B to 80° C. Add Part B slowly to Part A with agitation. Continue agitation until the mixture is congealed.

EXAMPLE 3

The following procedure may be adapted for the synthesis of all N-alkyl-N-retinoyl carbamic acid and N-aryl-N-retinoyl carbamic acid.

Synthesis of N-Phenyl-N-Retinoyl Carbamic Acid

All-trans-retinoic acid 1 gm is dissolved in 5 ml of dimethylsulfoxide, and phenylisocyanate 1 ml is added to the solution. After reacting at room temperature for 16 hours the mixture is slowly poured into 500 gm of cold water. Yellowish solid thus formed is filtered and is washed with water and alcohol. The product is recrystallized from acetone and water; yield is 0.8 gm.

N-phenyl-N-retinoyl carbamic acid thus synthesized is practically pure as shown by infrared spectroscopy and thin-layer chromatography with a mobility of 0.92 on a solvent system of methanol:benzene, 1:3.

N-phenyl-N-retinoyl carbamic acid may also be synthesized from retinoic acid and phenylisocyanate in dimethylformamide instead of in dimethylsulfoxide. The product is chemically identical as shown by infrared spectroscopy and thin-layer chromatography.

EXAMPLE 4

The following procedure may be used for the syntheses of all N-alkyl-N-retinoyl-thiocarbamic acid and N-aryl-N-retinoyl-thiocarbamic acid.

Synthesis of N-Phenyl-N-Retinoyl Thiocarbamic Acid

All-trans-retinoic acid 1 gm is dissolved in 5 ml of dimethylsulfoxide, and phenylisothiocyanate 1.2 ml is added to the solution. After reacting at 45° C. for 16 hours the mixture is slowly poured into 500 gm of cold water. The yellowish solid thus formed is filtered and is washed with water.

N-phenyl-N-retinoyl thiocarbamic acid thus synthesized is practically pure as shown by infrared spectroscopy and thin-layer chromatography with a mobility of 0.93 on a solvent system of methanol:benzene, 1:3.

EXAMPLE 5

Ethyl retinoyl lactate 0.2% cream is prepared as follows:

Ethyl retinoyl lactate 0.2 gm which is synthesized from all-trans-retinoic acid and ethyl lactate according to Example 1 is dissolved in 2 ml of acetone, and the solution admixed with 98 gm of hydrophilic ointment, USP. The mixing is continued until a uniform consistency is obtained. The therapeutic cream thus formulated may be stored in ointment jars.

EXAMPLE 6

Ethyl retinoyl glycolate 0.5% cream is prepared as follows:

Ethyl retinoyl glycolate 0.5 gm which is synthesized from all-trans-retinoic acid and ethyl glycolate, according to the method described in Example 1, is dissolved in 5 ml of acetone, and the solution admixed with 95 gm of hydrophilic ointment, USP. The mixing is continued until a uniform consistency is obtained.

EXAMPLE 7

Diethyl retinoyl tartrate 0.5% water-in-oil cream is prepared as follows:

Diethyl retinoyl tartrate 0.5 gm which is synthesized from all-trans-retinoic acid and diethyl tartrate, according to the method described in Example 1, is dissolved in 5 ml of acetone, and the solution admixed with 95 gm of water-in-oil cream formulated according to Example 2. The mixing is continued until a uniform consistency is obtained.

EXAMPLE 8

Triethyl retinoyl citrate 0.5% cream is formulated as follows:

Triethyl retinoyl citrate 0.5 gm which is synthesized from all-trans-retinoic acid and triethyl citrate, according to the method described in Example 1, is dissolved in 5 ml of acetone, and the solution admixed with 95 gm of hydrophilic ointment, USP. The mixing is continued until a uniform consistency is obtained.

EXAMPLE 9

Methyl retinoyl glycolate 0.5% water-in-oil cream is prepared as follows:

Methyl retinoyl glycolate 0.5 gm which is synthesized from all-trans-retinoic acid and methyl glycolate, according to the method described in Example 1 is dissolved in 5 ml of acetone, and the solution admixed with 95 gm of water-in-oil cream formulated according to Example 2. The mixing is continued until a uniform consistency is obtained.

EXAMPLE 10

Ethyl retinoyl mandelate 0.2% cream is prepared as follows:

Ethyl retinoyl mandelate 0.2 gm which is synthesized from all-trans-retinoic acid and ethyl mandelate according to the method described in Example 1, is dissolved in 2 ml of acetone, and the solution admixed with 98 gm of hydrophilic ointment, USP. The mixing is continued until a uniform consistency is obtained.

EXAMPLE 11

Methyl retinoyl salicylate 0.5% cream is prepared as follows:

Methyl retinoyl salicylate 0.5 gm which is synthesized from all-trans-retinoic acid and methyl salicylate, according to the method described in Example 1, is dissolved in 5 ml of acetone and the solution admixed with 95 gm of hydrophilic ointment, USP. The mixing is continued until a uniform consistency is obtained.

EXAMPLE 12

Isoamyl retinoyl mandelate 0.5% water-in-oil cream is prepared as follows:

Isoamyl retinoyl mandelate 0.5 gm which is synthesized from all-trans-retinoic acid and isoamyl mandelate, according to the method described in Example 1, is dissolved in 5 ml of acetone, and the solution admixed with 95 gm of water-in-oil cream formulated according to Example 2. The mixing is continued until a uniform consistency is obtained.

EXAMPLE 13

Retinoyl lactamide 0.2% water-in-oil cream is prepared as follows:

Retinoyl lactamide 0.2 gm which is synthesized from all-trans-retinoic acid and lactamide, according to the method described in Example 1, is dissolved in 2 ml of acetone, and the solution admixed with 98 gm of water-in-oil formulated according to Example 2. The mixing is continued until a uniform consistency is obtained.

EXAMPLE 14

Retinoyl glycolic acid 0.5% cream is prepared as follows:

Retinoyl glycolic acid 0.5 gm which is synthesized from all-trans-retinoic acid and glycolic acid, according to a modified method described in Example 1, is dissolved in 5 ml of acetone, and the solution admixed with 95 gm of hydrophilic ointment, USP. The mixing is continued until a uniform consistency is obtained.

EXAMPLE 15

Retinoyl phenyl lactic acid 0.5% cream is prepared as follows:

Retinoyl phenyl lactic acid 0.5 gm which is synthesized from all-trans-retinoic acid and beta-phenyl lactic acid, according to a modified method described in Example 1, is dissolved in 5 ml of acetone, and the solution admixed with 95 gm of hydrophilic ointment, USP. The mixing is continued until a uniform consistency is obtained.

EXAMPLE 16

Retinoyl salicylic acid 0.5% cream is prepared as follows:

Retinoyl salicylic acid 0.5 gm which is synthesized from all-trans-retinoic acid and salicylic acid, according to a modified method described in Example 1, is dissolved in 5 ml of acetone, and the solution admixed with 95 gm of hydrophilic ointment, USP. The mixing is continued until a uniform consistency is obtained.

EXAMPLE 17

Retinoyl salicylamide 0.5% water-in-oil cream is prepared as follows:

Retinoyl salicylamide 0.5 gm which is synthesized from all-trans-retinoic acid and salicylamide, according to the method described in Example 1, is dissolved in 5 ml of acetone, and the solution admixed with 95 gm of water-in-oil cream formulated according to Example 2. The mixing is continued until a uniform consistency is obtained.

EXAMPLE 18

N-phenyl-N-retinoyl-carbamic acid 1% water-in-oil cream is prepared as follows:

N-phenyl-N-retinoyl-carbamic acid 1 gm which is synthesized from all-trans-retinoic acid and phenylisocyanate according to Example 3 is directly admixed with 99 gm of water-in-oil cream formulated in compliance with Example 2. The mixing is continued until a uniform consistency is obtained.

EXAMPLE 19

N-ethyl-N-retinoyl-carbamic acid 0.5% lotion is prepared as follows:

N-ethyl-N-retinoyl-carbamic acid 0.5 gm which is synthesized from all-trans-retinoic acid and ethyl isocyanate according to the method described in Example 3 is dissolved in 5 ml of ethanol. The solution is admixed with 95 gm of a lotion prepared from mineral oil, cottonseed oil, isopropyl myristate and water with a surfactant such as sorbitan sesquioleate. The ingredients of said lotion are present in 15:15:10:55:5 parts by weight respectively.

EXAMPLE 20

N-allyl-N-retinoyl-carbamic acid 1% gel is prepared as follows:

N-allyl-N-retinoyl-carbamic acid 1 gm which is synthesized from all-trans-retinoic acid and allylisocyanate, according to the method described in Example 3, is dissolved in 70 ml of ethanol. The solution is admixed with 17 ml of water and 10 ml of propylene glycol. Hydroxypropylcellulose, 2 gm is added to the mixture with agitation. Continue agitation until a uniform gel is formed.

EXAMPLE 21

N-phenyl-N-retinoyl-thiocarbamic acid 1% water-in-oil cream is prepared as follows:

N-phenyl-N-retinoyl-thiocarbamic acid 1 gm is synthesized from all-trans-retinoic acid and phenylisothiocyanate, according to Example 4, is directly admixed with 99 gm of water-in-oil cream formulated in compliance with Example 2. The mixing is continued until a uniform consistency is obtained.

EXAMPLE 22

N-cyclohexyl-N-retinoyl-N'-cyclohexyl-carbamic amide may be synthesized as follows:

All-trans-retinoic acid 1 gm and N,N'-dicyclohexyl-carbodiimide 1 gm are dissolved in 7 ml of dimethylsulfoxide. The mixture is heated at 50° C. for 1 hour. The yellowish crystals thus formed are collected by filtration, and are washed with methanol. N-cyclohexyl-N-retinoyl-N'-cyclohexylcarbamic amide 1.4 gm thus synthesized is chemically pure as shown by infrared spectroscopy and thin-layer chromatography with a mobility of 0.89 on a solvent system of methanol:benzene, 1:9.

EXAMPLE 23

N-cyclohexyl-N-retinoyl-N'-cyclohexyl-carbamic amide 1% water-in-oil cream is prepared as follows:

N-cyclohexyl-N-retinoyl-N'-cyclohexyl-carbamic amide 1 gm which is synthesized according to Example 22 is directly admixed with 99 gm of water-in-oil cream formulated in accordance with Example 2. The mixing is continued until a uniform consistency is obtained.

THERAPEUTIC RESULTS

In order to evaluate the retinoyl compounds of this invention a total of more than 25 patients having psoriasis were treated with the compositions as follows:

Therapeutic compositions of retinoyl hydroxy-acids, retinoyl carbamic acid and retinoyl thiocarbamic acid in solution gel, lotion, cream or water-in-oil cream prepared according to the examples were topically administered to patients having psoriasis.

Treated areas were kept to minimal size convenient for topical applications: circles 4 cm in diameter demarcated with a plastic ring of that size inked on a stamp pad. The medicinal creams or ointments were topically applied by the patient in an amount (usually about 0.1 cubic millimeter) sufficient to cover the treatment site. Applications were made three times daily and without occlusive dressings. Application periods did not exceed two weeks, and applications were discontinued at any time when resolution of the lesion on the treatment area was clinically judged to be complete.

Generally, the affected skin of psoriasis became less scaly and less erythematous after a few days of topical treatment. The scaly and erythematous lesions ordinarily were substantially restored to normal appearing skin after one to two weeks treatment. The sites of the lesions, devoid of any scales, usually reached an improved state comparable to normal skin within two weeks after initial treatment. The results on psoriatic patients are summarized in the following tables.

| Effects on Psoriasis of Topical Retinoyl Hydroxy Acids and Derivatives | | |
|---|---|---|
| Compounds | Number of Patients | Therapeutic Effectiveness |
| Ethyl retinoyl lactate | 4 | 3+ |
| Ethyl retinoyl glycolate | 4 | 3+ |
| Diethyl retinoyl tartrate | 4 | 3+ |
| Methyl retinoyl glycolate | 4 | 3+ |
| Triethyl retinoyl citrate | 6 | 4+ |
| Methyl retinoyl salicylate | 4 | 3+ |
| Isoamyl retinoyl mandelate | 6 | 4+ |
| Ethyl retinoyl mandelate | 4 | 3+ |
| Retinoyl lactamide | 3 | 4+ |
| Retinoyl glycolic acid | 4 | 3+ |

3+ Disappearance of scale from lesions
4+ Restoration to normal looking skin.

| Compound | Number of Patients | Therapeutic Effectiveness |
|---|---|---|
| N-phenyl-N-retinoyl-carbamic acid | 7 | 4+ |
| N-allyl-N-retinoyl-carbamic acid | 6 | 3+ |
| N-ethyl-N-retinoyl-carbamic acid | 6 | 3+ |
| N-propyl-N-retinoyl-carbamic acid | 6 | 3+ |
| N-m-chlorophenyl-N-retinoyl-carbamic acid | 4 | 3+ |
| N-butyl-N-retinoyl-carbamic acid | 4 | 3+ |
| N-allyl-N-retinoyl-thiocarbamic acid | 3 | 3+ |
| N-phenyl-N-retinoyl-thiocarbamic acid | 3 | 3+ |
| N-cyclohexyl-N-retinoyl-N'-cyclohexyl-carbamic amide | 3 | 3+ |

Effects of Psoriasis of Topical Retinoyl Carbamic Acid, Retinoyl Thiocarbamic Acid and Derivative 3+ Disappearance of scale from lesions
4+ Restoration to normal looking skin.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are, therefore, intended to be embraced herein.

What is claimed is:

1. A method of alleviating the symptoms of psoriasis in humans comprising topically applying to involved areas of the human body an effective amount of a composition comprising:
   a therapeutically effective amount of at least one compound having the formula:

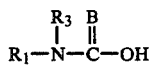

wherein
   $R_1$ = retinoyl ($C_{20} H_{27} O$);
   $R_3$ = H, alkyl or aryl having from 1 to 20 carbon atoms; and
   B = O or S, or salt thereof formed with organic or inorganic alkalis, in a pharmaceutically acceptable vehicle.

2. The method of claim 1 wherein said member is present in a concentration of from 0.01 to 5% by weight of the total composition.

3. The method of claim 1 wherein a plurality of said compounds are present in a concentration range of from 0.02 to 2% by weight of the total composition.

4. The method of claim 1 wherein said compound is N-methyl-N-retinoyl-carbamic acid.

5. The method of claim 1 wherein said compound is N-ethyl-N-retinoyl-carbamic acid.

6. The method of claim 1 wherein said compound is N-propyl-N-retinoyl-carbamic acid.

7. The method of claim 1 wherein said compound is N-butyl-N-retinoyl-carbamic acid.

8. The method of claim 1 wherein said compound is N-allyl-N-retinoyl-carbamic acid.

9. The method of claim 1 wherein said compound is N-phenyl-N-retinoyl-carbamic acid.

10. The method of claim 1 wherein said compound is N-octadecyl-N-retinoyl-carbamic acid.

11. The method of claim 1 wherein said compound is N-m-chlorophenyl-N-retinoyl-carbamic acid.

12. The method of claim 1 wherein said compound is N-p-tolyl-N-retinoyl-carbamic acid.

13. The method of claim 1 wherein said compound is N-m-tolyl-N-retinoyl-carbamic acid.

14. The method of claim 1 wherein said compound is N-o-tolyl-N-retinoyl-carbamic acid.

15. The method of claim 1 wherein said compound is N-methyl-N-retinoyl-thiocarbamic acid.

16. The method of claim 1 wherein said compound is N-ethyl-N-retinoyl-thiocarbamic acid.

17. The method of claim 1 wherein said compound is N-butyl-N-retinoyl-thiocarbamic acid.

18. The method of claim 1 wherein said compound is N-allyl-N-retinoyl-thiocarbamic acid.

19. The method of claim 1 wherein said compound is N-phenyl-N-retinoyl-thiocarbamic acid.

20. The method of claim 1 wherein said compound is N-cyclohexyl-N-retinoyl-thiocarbamic acid.

21. A method of alleviating the symptoms of psoriasis in humans comprising topically applying to involved areas of the human body an effective amount of a composition comprising:
    a therapeutically effective amount of N-cyclohexyl-N-retinoyl-N'-cyclohexyl-carbamic amide in a pharmaceutically acceptable vehicle.

22. The method of claim 21, wherein said compound is present in a concentration of from 0.01 to 5% by weight of the total composition.

23. An antipsoriatic composition for topical application to the human body comprising:
    an effective amount of at least one compound of the formula

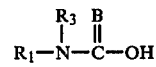

wherein
    $R_1$ = retinoyl ($C_{20} H_{27} O$);
    $R_3$ = H, alkyl or aryl having from 1 to 20 carbon atoms; and
    B = O or S, or salt thereof formed with organic or inorganic alkalis, in a pharmaceutically acceptable vehicle for topical application.

24. The composition of claim 23 wherein said member is present in a concentration of from 0.01 to 5% by weight of the total composition.

25. The composition of claim 23 wherein said composition comprises a plurality of said compounds present in a concentration of from 0.02 to 2% by weight of the total composition.

26. The therapeutic composition of claim 23 wherein said compound is N-methyl-N-retinoyl-carbamic acid.

27. The therapeutic composition of claim 23 wherein said compound is N-ethyl-N-retinoyl-carbamic acid.

28. The therapeutic composition of claim 23 wherein said compound is N-propyl-N-retinoyl-carbamic acid.

29. The therapeutic composition of claim 23 wherein said compound is N-butyl-N-retinoyl-carbamic acid.

30. The therapeutic composition of claim 23 wherein said compound is N-allyl-N-retinoyl-carbamic acid.

31. The therapeutic composition of claim 23 wherein said compound is N-phenyl-N-retinoyl-carbamic acid.

32. The therapeutic composition of claim 23 wherein said compound is N-octadecyl-N-retinoyl-carbamic acid.

33. The therapeutic composition of claim 23 wherein said compound is N-m-chlorophenyl-N-retinoyl-carbamic acid.

34. The therapeutic composition of claim 23 wherein said compound is N-p-tolyl-N-retinoyl-carbamic acid.

35. The therapeutic composition of claim 23 wherein said compound is N-m-tolyl-N-retinoyl-carbamic acid.

36. The therapeutic composition of claim 23 wherein said compound is N-o-tolyl-N-retinoyl-carbamic acid.

37. The therapeutic composition of claim 23 wherein said compound is N-methyl-N-retinoyl-thiocarbamic acid.

38. The therapeutic composition of claim 23 wherein said compound is N-ethyl-N-retinoyl-thiocarbamic acid.

39. The therapeutic composition of claim 23 wherein said compound is N-butyl-N-retinoyl-thiocarbamate acid.

40. The therapeutic composition of claim 23 wherein said compound is N-allyl-N-retinoyl-thiocarbamic acid.

41. The therapeutic composition of claim 23 wherein said compound is N-phenyl-N-retinoyl-thiocarbamic acid.

42. The therapeutic composition of claim 23 wherein said compound is N-cyclohexyl-N-retinoyl-thiocarbamic acid.

43. An antipsoriatic composition for topical application to the human body comprising:
an effective amount of N-cyclohexyl-N-retinoyl-N'-cyclohexyl-carbamic amide in a pharmaceutically acceptable vehicle for topical application.

44. The composition of claim 43 wherein said compound is present in a concentration of from 0.01 to 5% by weight of the total composition.

* * * * *